(12) United States Patent  
Pegram et al.

(10) Patent No.: US 6,636,812 B2  
(45) Date of Patent: *Oct. 21, 2003

(54) PARTICULATE COMPOSITIONS

(75) Inventors: Stephen C. Pegram, Jacksonville, FL (US); Scott P. Klein, Lake Wales, FL (US); Christopher L. Davidson, Marysville, WA (US); Stanley A. Patterson, Lithia, FL (US); Thomas L. Coulter, Lakeland, FL (US); John R. Schmedeman, Bartow, FL (US)

(73) Assignee: Cargill, Incorporated, Wayzata, MN (US)

( * ) Notice: Subject to any disclaimer, the term of this patent is extended or adjusted under 35 U.S.C. 154(b) by 207 days.

This patent is subject to a terminal disclaimer.

(21) Appl. No.: 09/768,179

(22) Filed: Jan. 23, 2001

(65) Prior Publication Data

US 2001/0027379 A1 Oct. 4, 2001

Related U.S. Application Data

(63) Continuation of application No. 09/060,596, filed on Apr. 15, 1998, now Pat. No. 6,178,383.

(51) Int. Cl.[7] ............................................. G01N 29/00
(52) U.S. Cl. ...................... 702/25; 702/22; 73/863.41; 73/864.21; 356/417
(58) Field of Search ............................ 702/22, 24, 25, 702/31; 73/863.41, 863.51, 863.71, 864.21, 864.22; 356/417, 441, 442; 250/226, 574

(56) References Cited

U.S. PATENT DOCUMENTS

| | | | | |
|---|---|---|---|---|
| 4,797,550 A | * | 1/1989 | Nelson et al. | 250/226 |
| 5,396,260 A | * | 3/1995 | Adel et al. | 345/91 |
| 6,178,383 B1 | * | 1/2001 | Pegram et al. | 702/25 |

* cited by examiner

Primary Examiner—Bryan Bui  
(74) Attorney, Agent, or Firm—Jeff Skelton (57) ABSTRACT

An on-line sampling and analysis system and method in which a sampling line inlet pipe receives a continuous flow of a suspension or a slurry having particulates, such as grains, seed or phosphate rock, for rapid analysis of the contents therein in a flowing stream. A sample presentation area such as a window is positioned below the flow of the suspension or slurry in an assembly allowing for the depositing of a sample of solid content from the suspension or slurry which is collected for viewing by a computer controlled video camera. The camera is provided for imaging the sample of the solid content collected at the sample presentation area, and a personal computer analyzes images provided by the camera to characterize the content of the fluid media. A media flow director positioned in the suspension or slurry flow through the assembly, and above the sample presentation area, generates a vortex for removing the sample of the solid content deposited on the sample presentation area, allowing for the collection of another sample from the suspension or slurry at the sample presentation area. The vortex tube is coupled with associated bypass piping to remove the sample from the system, or return the solid content sample to the flow of the fluid suspension or slurry downstream of the sample presentation area for continuous operation without interruption of the flow in the sampling line. The personal computer provides a user interface for monitoring the content of the suspension or slurry.

32 Claims, 6 Drawing Sheets

```
P000  +--+--|/|--+--|/|---------------------( )--+ ─60
      |    I/6  |   I/7              B/0        |
      +--| |--+                                  |
      |   B/0                                    |
      |                                          |
P001  +--| |----|/|-----------------|TON 0|--+
      |   B/0   T03/DN              |2 sec |  |
      |                                        ─62
P002  +--| |----|/|-------------------( )----+
      |  T0/EN  T0/DN                   0/1  |
      |                                      |
P003  +--| |----|/|-----------------|TON 01|-+
      |  T0/DN  T03/DN              | 2 sec|  |
      |                                        ─64
P004  +--| |----|/|-------------------( )----+
      | T0/EN   T1/DN                   0/2  |
      |                                      |
P005  +--| |----|/|-----------------|TON 02|-+
      |  T1/DN  T03/DN              |0.5 sec| |
      |                                        ─66
P006  +--| |----|/|-------------------( )----+
      | T2/EN   T2/DN                   0/3  |
      |                                      |
P007  +--| |------------------------|TON 03|-+
      |  T2/DN                      |0.1 sec| |
      |                                        ─68
P008  +--| |----|/|-------------------( )----+
      |T03/EN  T03/DN                   0/4  |
      |                                      |
      +                                      +
```

INPUT/OUTPUT

| | |
|---|---|
| I/6 | Cycle start input (not used) |
| I/7 | Cycle stop input (not used) |
| B/0 | Internal bit used for "Latching" the start signal. |
| 0/1 | Control relay for "Pinch valve open" command. |
| 0/2 | Control relay for "Settling time". |
| 0/3 | Control relay for "Image ready" command. |
| 0/4 | Control relay for "Analytical wait timer". |
| Tx/EN | Timer "x" Enabled bit. |
| Tx/DN | Timer "x" Done bit. |

FIG. 3

Picture grab from IPPD IMAGE sampler.

PARTICULATE COMPOSITIONS

This is a continuation, of prior application Ser. No. 09/060,596, filed Apr. 15, 1998, now U.S. Pat. No. 6,178,383, which is hereby incorporated herein by reference in its entirety.

BACKGROUND OF THE INVENTION

1. Field of the Invention

The present invention relates in general to on-line sampling and analysis of a solid particulate suspended in a fluid, such as a phosphate rock, other minerals, grains, seed and other solids suspended in water, air, or other liquids or gases. More particularly, the invention relates to positioning a vortex tube in a process stream above a sample presentation area such as a light transparent window for removing deposited particulates, such as phosphates, and allowing for the collection of subsequent samples, in which the vortex tube provides a bypass to return the particulate samples to the flow downstream of the sample presentation area for continuous operation without interruption of the flow in the sampling line.

2. Description of the Related Art

Presently, phosphate rock is recovered from a sand-clay mixture that is mined from mineral deposits. Industrial recovery of solids of a few millimeters or less, such as phosphate rock, e.g., <1 mm, begins with chemical treatment of a liquid aqueous slurry which includes a long chain hydrocarbon liquid. These hydrocarbons attach to the phosphate rock and are hydrophobic in nature. Thus, after they attach to the rock, the phosphate rock is forced out of the water phase to the surface in an aeration tank called a flotation cell. The flotation cell must be monitored to ensure maximum recovery of the phosphate rock. The phosphate content in the slurry exiting the flotation cell after the removal of the hydrocarbon-bound phosphate rock, also known as tailings, is a representative indicator of flotation cell performance.

Phosphate rock found in the tailings is considered unrecoverable and a lost natural resource. Normal operation of the flotation cell involves operator estimation of cell performance by visual inspection of the tailings. To optimize the operator's control of the flotation cell, it would be desirable therefore to provide a system and a method of continuously monitoring phosphate tailings to provide feedback to the operator to improve the performance and efficiency of the flotation cell operation. To this end, it is usually desirable to maintain the %BPL content in the tailings streams below 3% for acceptable cell performance.

U.S. Pat. No. 5,396,260 to Adel et al. for "Video Instrumentation for the Analysis of Mineral Content in Ores and Coal" issued Mar. 7, 1995, discloses the determination of mineral content using a video system in which digitized images having assigned gray levels are analyzed to determine the content of particular minerals in a coal slurry determined from the distribution of the gray levels. Slip streams are extracted from the tailings and feed lines which are allowed to pass through a thin sample chamber with flat glass plates on either side, the sample chamber being enclosed in a light type box with a video camera to provide a reflected light image for sample analysis. However, such slip streams extracted from the tailings and feed lines, are not in line with the tailings stream but merely tapped away from the fluid media being processed and may not be representative of the sampling of an on-line flowing slurry.

U.S. Pat. No. 4,797,550 to Nelson et al. for "Fiber Optic Detector for Flotation Cell Processing" issued Jan. 10, 1989 discloses a fiber optic detector submerged in a coal slurry to monitor a coal separation process. Light transmitted by an optical fiber is directed toward the slurry, and thus scattered by the slurry, from which a portion of the light is deflected back to the fiber optic detector, from which the light intensity reflected by the slurry is used to detect the mineral content in the slurry. Accordingly, only a small sample separated from the slurry is analyzed, which may not be representative of the on-line stream.

It would be desirable therefore to provide on-line sampling in which sampling of the particulate content in a fluid media is provided in-line with the process stream to collect representative particulate samples, such as phosphate rock and sand in a tailings line. An in-line sample presentation assembly would be advantageous for the collection of samples from the tailings where the sample could be returned to a slurry stream for continuous operation without interruption of the flow in the sampling line.

SUMMARY OF THE INVENTION

Typical particulate analysis techniques provide off-line analysis or tapping of relatively small representative samples of the particulates suspended in a fluid media. These are often difficult to correlate to current process conditions from the resultant data. An on-line analyzer provides faster and better feedback for adjusting process control parameters. The apparatus and method embodying the present invention provides on-line sampling and analysis of the content of a particulate composition having a particle size from about 0.1 to about 20 mm, which is suspended or slurried in a fluid, which may be a liquid or a gas, to provide a rapid analysis of the particulate composition. The use of the fluid stream discussed herein is generic to gas and liquid carrier media. In an important aspect, the invention provides a method and apparatus for the analysis of the phosphate rock content values in a flowing slurry stream. The phosphate analyzer is provided in-line with the tailings stream of a phosphate floatation process.

In one aspect, the method of invention employs visual light and a visual light characterizing detection device which uses a visual image of the particulates, such as grains or seed in suspension or a phosphate tailings slurry, to analyze the particulate sample. The on-line sampling apparatus collects and presents samples that are rapidly purged and resampled using a procedure in which particulate solids in a fluid stream in gas or liquid are accumulated, concentrated or packed in a vessel or container for in-line analysis. In another aspect the characterizing detection device used to analyze the samples may use X-ray, gamma-ray, neutron, alpha particle, or other radiation sources other than visual light where a sample is presented on an area not transparent to visual light, but which is transparent to the energy source. In a further aspect the characterizing detection device may employ magnetic, acoustic, ultra-sound, or other energy sources where the particulate sample is presented in a sample presentation area which is analyzed with the particulate sample packed for the application of the associated energy or force. Analysis using electromagnetic energy such as X-ray, ultra-violet, infra-red or other radiation sources other than visual light requires a sample presentation area with a window transparent to the energy being used. Another important aspect provides optical image analysis using a video camera normal to the sample deposited on the sample presentation area using a computer providing image processing of the samples. To capture this image, an in-line mechanical delivery vortex assembly presents a representative sample to a video camera. The invention provides a uniform, stationary, and quickly removable particulate sample which is trapped and imaged by positioning a vortex tube in the process stream above the particulate sample presentation area for thereafter removing deposited particulates. The invention allows for the collection of subsequent particulate samples, in which the vortex tube provides a bypass to return samples to the flow downstream of the sample presentation area. In the invention, the particulate sample being analyzed is taken from the continually flowing stream of particulates suspended in the fluid media to provide a representative particulate sample without interruption of the flow.

According to the invention, the in-line analysis system introduces a sample of suspended or slurried particulate composition, such as a sand, phosphate, and water slurry stream into a vortex assembly. The slurry stream gravitationally deposits a particulate layer, such as sand and particulate phosphate on the bottom of the vortex assembly, which can be viewed through a quartz imaging window. In an important aspect this window is a substantially planar surface to present a sample which has a planar surface to the characterizing detection device. Pressure-inducing piping, located downstream of the vortex assembly slightly restricts the flow of this stream, yet permits an uninterrupted flow of slurry through the system while allowing the deposited sample to be stationary for optical detection or analysis during each sampling cycle. In an important aspect, analysis is done by an imaging technique. When a new sample and sample image is needed, the deposited layer is removed by opening a bypass line around the pressure restriction. The pressure released causes a vortex that removes the old sample and allows a subsequent portion of the flow stream to be sampled. When the bypass valve is closed, the new sample is quickly and uniformly gravitationally deposited on the quartz viewing glass.

In one aspect, the particulate layer, such as sand and phosphate, is deposited on the quartz sample presentation area which is transparent or pervious to light. The sample is imaged through this viewing glass with a black-and-white or color video camera. The camera captures still images for analysis, and when a new image is required, the bypass valve is opened and closed again. The signal from the camera is captured by a frame grabber computer card which translates the picture into a pixel matrix image. The computer software determines the average pixel gray-scale or color value, which is compared with a standard associated with phosphate content. To verify the correlation, the computer also analyzes individual particle sizes, which information is used to correct the standard for shifts in gray-scale or color of the particulates which in the case of phosphates, the sand and slurry matrix may change continuously due to the nature of mineral deposits. A computer-user interface is provided for displaying the current image, the analyses information, such as calculated phosphate content, particle size information, and historical trends.

The invention provides an on-line sampling and image analysis apparatus for analyzing various compositions of fluid media having suspended particulates. The fluid media may be a gas, or in an important aspect, a liquid such as water, and the particulates may include rock, sand or other solid particle content. A media flow director such as the vortex assembly directs the media over the sample presentation area to remove the deposited particulates.

In an important aspect, an on-line sampling and image analysis system has an inlet pipe for receiving a continuous flow of a slurried particulates. A sample presentation area is positioned below the flow of the slurry in an assembly allowing for the depositing of a sample of particulates from the slurry which is collected for viewing by a computer controlled video camera. Gravity settles the particles onto the sample presentation area. The camera images the sample of the particulate solid deposited on the sample presentation area which is a light transparent window, and a personal computer analyzes images provided by the camera to characterize the particulate composition in the fluid media. A vortex tube positioned in the flow of the slurried particulate through the assembly, and above the sample presentation area, generates a vortex for removing the sample of the particulates deposited on the sample presentation area, allowing for the collection of a subsequent sample from the slurry at the sample presentation area. The vortex tube is coupled with associated bypass piping to remove the particulate sample from the flow, or to return the particulate sample to the flow of the fluid slurry downstream of the sample presentation area for continuous operation without interruption of the flow in the sampling line. The personal computer provides a user interface for monitoring the phosphate content of the slurry.

Briefly summarized, the present invention is directed to an on-line particulate sampling and analysis system and method in which a sampling line inlet pipe receives a flow of a liquid or gas fluid media having a particulate solid content suspended therein. A sample presentation area is positioned below the flow of the fluid media in an assembly allowing for the depositing of a sample of the particulates from the fluid media. The sampled solid content is thus collected for viewing in order to characterize the particulate solid in the fluid media. In an important aspect, a vortex tube positioned above the sample presentation area generates a vortex for removing the particulate sample deposited on the sample presentation area, allowing for the collection of another particulate sample from the fluid media at the sample presentation area. The vortex tube may be coupled with associated bypass piping to remove the particulate sample from the flow, or to return the particulate sample to the flow of the fluid media downstream of the sample presentation area for continuous operation without interruption of the flow in the sampling line.

It is an object of the present invention to provide analysis on-line sampling and analysis of a particulate solid content suspended in a fluid media that overcomes the disadvantages and problems of the prior art.

It is another object of the invention to provide an on-line sampling and image analysis system and method for particulate solids, such as the phosphate content in a process stream.

It is a further object of the invention to provide positioning of a vortex tube in a process stream above a sample presentation area for removing deposited particulates allowing for the collection of subsequent particulate samples.

It is yet another object of the invention to provide a vortex tube coupling to a bypass pipe to remove the particulate sample from the flow, or to return particulate samples to the flow downstream of the sample presentation area for continuous operation without interruption of the flow in the sampling line.

Other objects and advantages of the present invention will become apparent to one of ordinary skill in the art, upon a perusal of the following specification and claims in light of the accompanying drawings and appendix.

DETAILED DESCRIPTION OF THE EMBODIMENTS OF THE INVENTION

Figure 1:
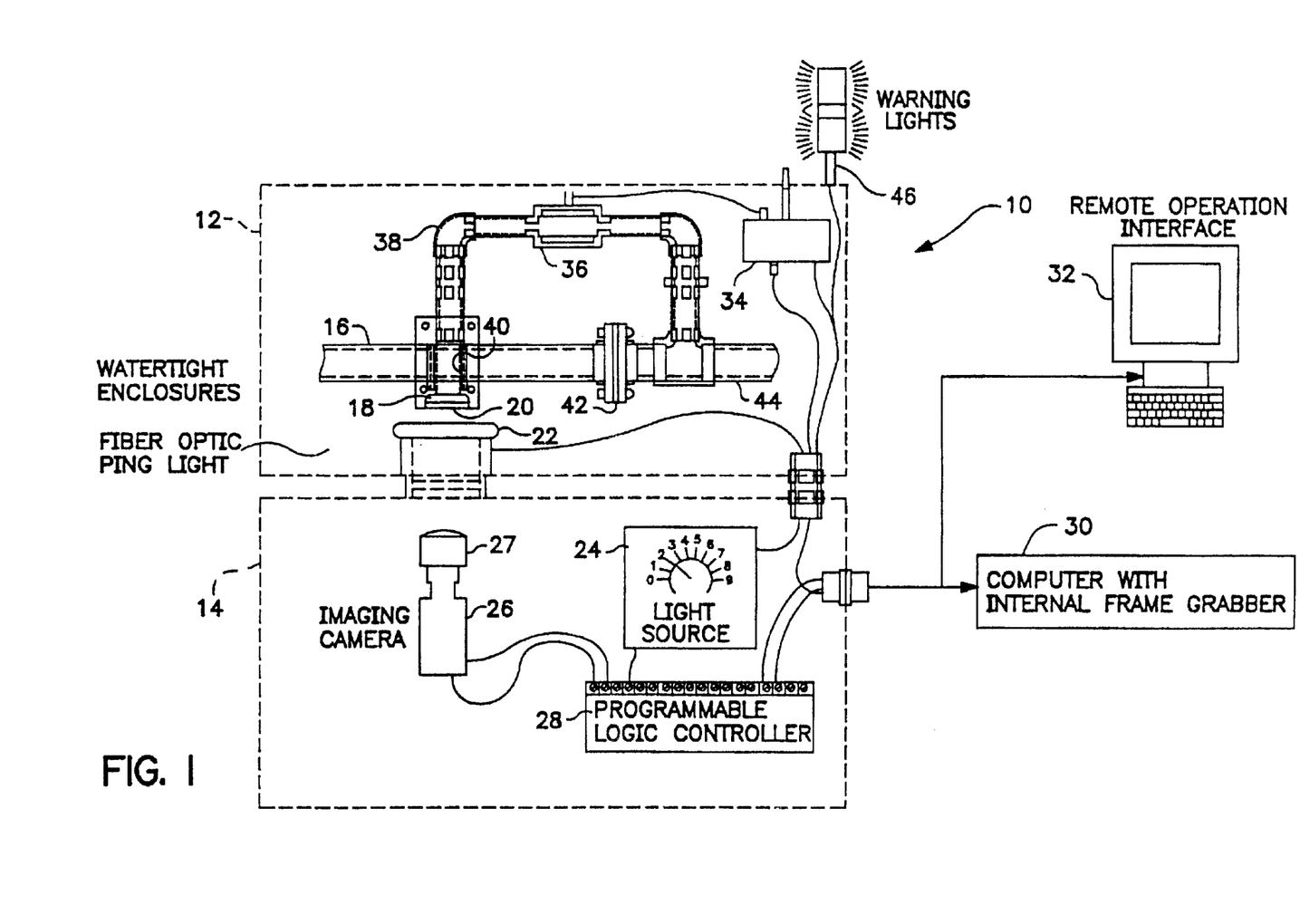
FIG. 1 shows an on-line system for determining %BPL analysis of phosphate rock materials embodying the present invention.
Figure 2:
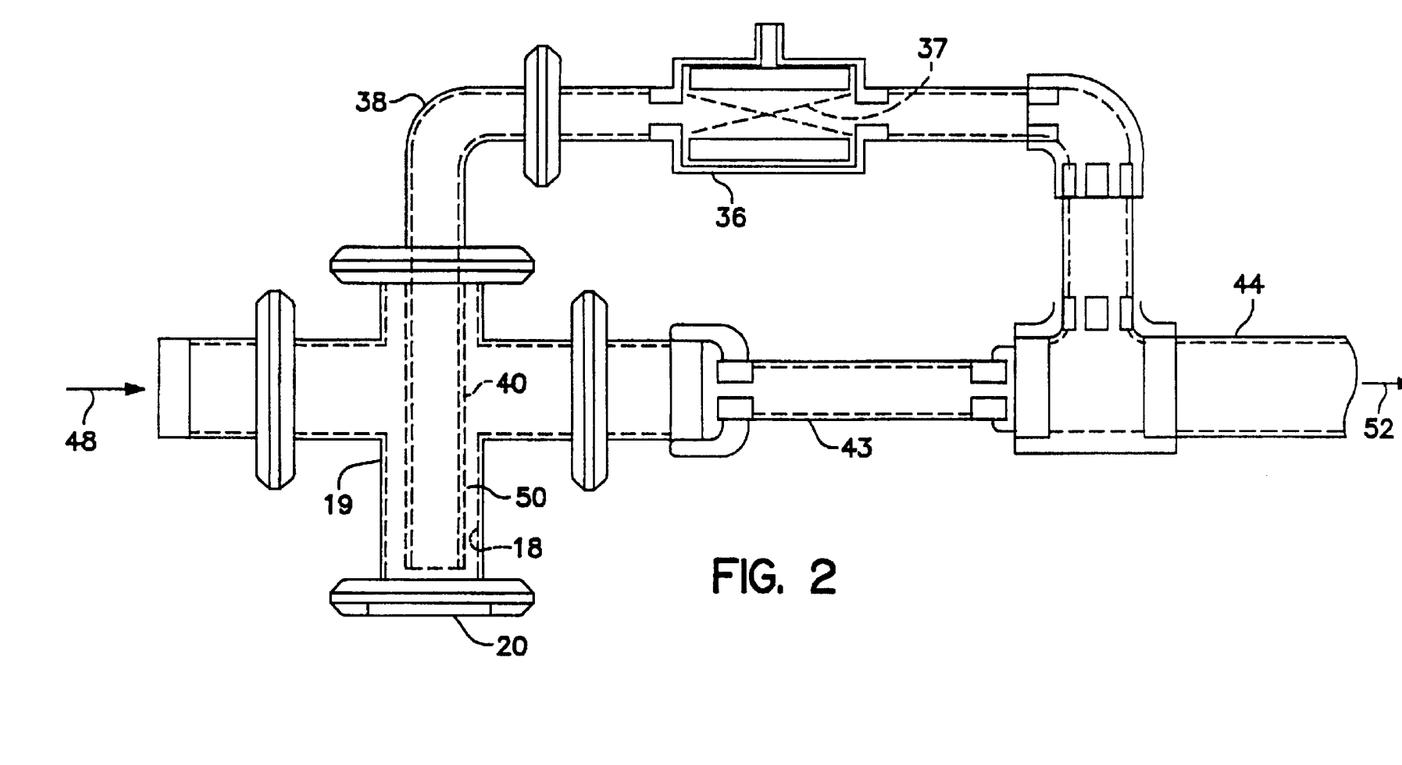
FIG. 2 is the sampling and image analyzing vortex assembly of the system shown in FIG. 1.

Referring now to the drawings and especially to FIGS. 1 and 2, FIG. 1 shows and on-line system 10 for determining the %BPL analysis of phosphate rock material embodying the present invention. The sampling system 10 performs optical detection, wherein an important aspect of the embodiment employs optical image analysis of particulates such as a solid content suspended in a slurry for sampling in an in-line vortex assembly 12 of the system 10. The imaging and controller electronics are housed in a separate watertight enclosure 14 which is coupled to the watertight enclosure of the vortex assembly 12 with dust boot seals, herein Heeco Protecto Boots. Watertight enclosures manufactured by the Hoffman Company were found acceptable in the in-line mill and mining applications described herein. An inlet pipe 16 introduces a liquid slurry to the assembly 12 for receiving the fluid media having solid particulates suspended therein. The pipe assembly through which the fluid media is directed includes a cavity 18 below the directed flow of the fluid media. A sample presentation area, herein a sample presentation window 20, wherein a sight glass view port provided by Quartz Scientific Inc. positioned at the bottom of the cavity 18, which may be formed with the cross pipe 19 of FIG. 2 is provided for collecting the samples of the solid particulate content from the fluid media in the cavity 18 of the pipe assembly for viewing through the sample presentation window 20.

The solid particulate content is collected on the presentation window 20, wherein an important aspect of the described embodiment employs gravitational depositing of the sample from the fluid media into the cavity 18 below. A variety of tests indicated satisfactory analysis, e.g. with phosphate rock slurries in water, and seed or grain suspended in air such as birdseed which included seed of various sizes. Thus grains on the order of approximately 0.1 to 20 mm may be characterized. A fiber optic light ring 22 is coupled to a light source 24, part number TQ-F01-1, both the light source 24 and the compatible fiber optic light ring 22 being provided by Micro Optics of Florida for high intensity illumination of the sample with the light ring 22. The imaging camera 26, Javelin part number JE3662HR is equipped with a zoom 7000-microzoom lens 27 provided by Micro Optics of Florida provides an appropriate optical detector, however, other means of optical detection may also be incorporated, such as ultraviolet and infrared lighting and other energy sources also may be used for analysis such as that of gamma ray-neutron and magnetic resonance analyzers or the like. Gamma ray-neutron analyzers such as the Australian Mineral Development Labs (AMDEL) equipment or magnetic resonance analyzing equipment, e.g., a "Phospholyzer" device of Harrison R. Cooper Systems, Inc., AMF Box 22014, Salt Lake City, Utah 84122 may be used as characterizing detection devices.

The light source 24 and imaging camera 26 are coupled to a programmable logic controller (PLC), herein an Allen Bradley model AB Micrologic 1000 PLC control interface, which is further coupled to a computer, herein a 200 megahertz Pentium-based personal computer 30 having internal frame grabber hardware. Additionally, a remote operator interface 32 may be provided for monitoring the in-line sampling and imaging process. The PLC 28 is coupled to a pneumatic control valve 34 of the vortex assembly 12 for controlling the compatible pneumatic pinch valve 36, herein a 1" pneumatic pinch valve 49155K23 provided by Red Valve, Inc. The pneumatic pinch valve 36 of the assembly 12 is coupled with piping 38 to a media flow director such as a vortex tube 40 which extends through the flow of the fluid media into the cavity 18, above the central presentation window 20. The flow of the fluid media to the assembly 12 is provided through a primary path in which the differential pressure orifice 42, herein a ceramic ¾" orifice, or a restricted pipe 43 for limiting the flow through the 2" pipe of the assembly 12 as the flow proceeds towards an outlet pipe 44.

The PLC 28 controls the sequencing of the pinch valve 36 to provide a bypass of the primary flow through the vortex tube 30 coupled to the pinch valve 36 as an additional flow of the fluid media toward the outlet pipe 34. One of the indicators, such as warning light 46 may be provided under control of the computer 30 to indicate an alarm condition when the phosphate content of the liquid slurry exceeds the predetermined limit identified by analyzing the images of the samples to characterize the solid content of the fluid media collected at the sample presentation window 20.

Turning now to FIG. 2, the sample and image analyzing vortex assembly 12 provides the media flow director therein which directs a flow 48 received in inlet pipe 16 as the fluid media proceeds in the flow direction to outlet 44 through the assembly 12, the solid particulate components of the slurry fall out of the fluid media into an annulus 50 formed by the outer diameter of the vortex tube 40. The inner diameter of the cavity 18 allows the solid particulates to deposit and collect on the sample presentation window 22 for analysis through a view imaging view port. To this end, the width of the annulus 50 should be no less than three times that of the greatest solid particulate so as not to clog the annulus 50 and allow the solid particulates through the annulus 50. The positioning of the vortex tube 40 in the cavity 18 is provided with a steel or glass assembly, or alternatively a cross pipe section 19 as in FIG. 2. Thus, as the flow 48 proceeds through the vortex tube interconnection and the differential pressure orifice 42 towards the outlet 44 in the outlet flow direction 52, when the pinch valve 36 is shown as open, the bypass coupled through pipe 38 allows for relatively higher pressure flow through the bypass so as to cause a vortex in the vortex tube 40 for removing the sample of the solid particulate content collected at the sample presentation window 20. When, however, the pneumatic pinch valve is in its closed position, as shown by reference numeral 37, the bypass through pipe 38 is inhibited, and the flow 48 proceeds directly through its primary path to outlet 44 without the generation of a vortex. The timing of the opening and closing of the pinch valve, as indicated by reference numerals 36 and 37, respectively, is sequenced by the PLC 28 providing for rapid repetitive sampling of the particulates flowing through assembly 12. This periodic sampling may be provided on the order of seconds, specifically 3 second samples, but the timing may be increased to provide sampling on the order of minutes, described further below in connection with the personal computer interface of FIG. 6.

As described, the differential pressure provided between the bypass and the primary flow direction of the fluid media out towards the outlet pipe 34 allows for the generation of the vortex in the vortex forming tube 40 of the apparatus 12 when the bypass 38 coupled to the pneumatic pinch valve is opened. A need for providing the differential pressure between the bypass and primary path, such as the differential pressure orifice 42 or a restrictive portion of a piping in the primary path provides for the differential pressure allowing for the creation of the vortex in the tube 40 as the flows exit the system 10 in the flow direction 52 of the assembly 12. Accordingly, the tube 40 forming the vortex is coupled for returning the sample of the solid content collected within the cavity 18 on the sample presentation window 20 to the fluid media 52 at the outlet pipe 44 downstream of the sampling cavity 18. Thus, the PLC 28 under control of the computer 30, controls the camera 26 and the pneumatic pinch valve 36 for sequencing the operation of the system 10 for removing the deposited solid particulate content samples allowing for the collection of subsequent samples in which the vortex tube 40 provides a bypass via pipe 38 to return the samples to the flow 52 downstream of the sample presentation window 20 for continuous operation without interruption of the flow in the sampling line.

Figure 3:
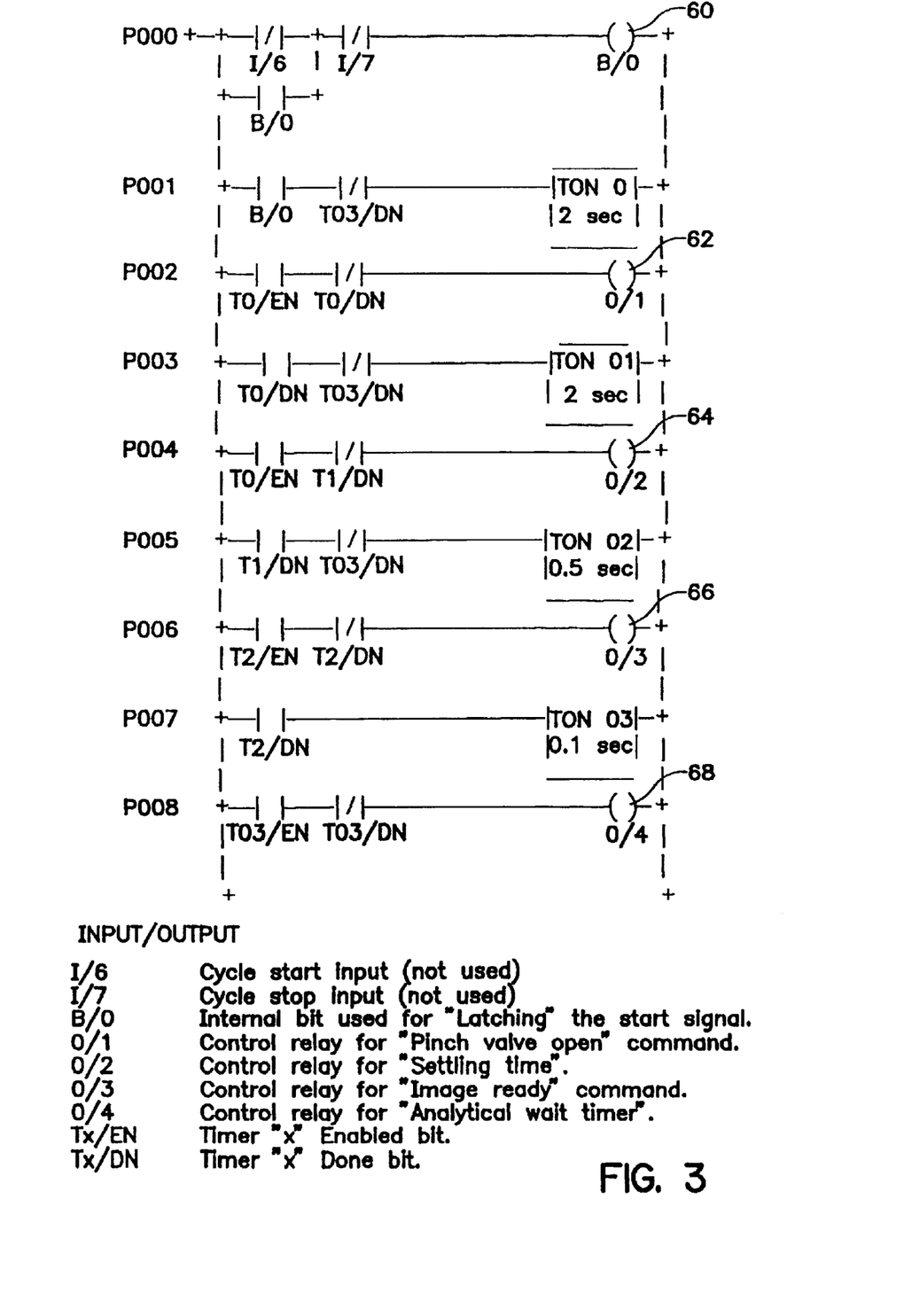
FIG. 3 is a programmable logic controller (PLC) ladder logic program for the PLC shown in FIG. 1.

To this end, a programmable logic controller ladder logic program for the PLC 28 is shown in FIG. 3, in which the sequencing of the latching of a start signal 60 initiates the timing provided by the PLC 28. At reference 62 of the ladder logic, an output signal is provided for indicating the pinch valve open command which is followed by a settling time provided at 64. Following the settling time of approximately two seconds, an image ready command is initiated as an output signal from the PLC 28 at reference 66. An analytical wait timer 68 is provided in the PLC 28 ladder logic for allowing the personal computer 30 to perform the necessary analysis on the acquired image sample. Subsequent processing of the ladder logic program indicated in FIG. 3 provided for continuous acquisition of samples and analysis in the system 10, as described.

During the sampling process, the computer 30 and air valve 36 operations are timed in FIG. 3 in order to capture still images for analysis. When the valve 36 is open, a new sample is being obtained as the camera 26 images a swirling motion. When the valve is closed, the slurry stops swirling and rapidly settles by the forces of gravity on the sight glass 20. To capture an accurate image, the frame grabber inside the computer 30 acquires the image after the solid particulates, e.g., sand, settles on the sight glass 20. To synchronize the time between the computer 30 and valve 36, the design programmed the PLC 28 to operate in four areas of timing. The first time delay represents the time the valve is open and acquiring a new sample. The second time delay is used to allow the solids to settle on the sight glass 20. During the third time delay, the PLC 28 sends a signal to the computer 30, via the serial port, to indicate that an image is ready to be captured. The fourth time delay represents a buffer period when the PLC 28 stops sending the signal to the computer 30 while the valve 36 remains in closed position 37. This buffer period protects the computer 30 against the possibility of grabbing an image when the valve 36 is beginning to open. These four time delays are run in an infinite loop on the PLC 28. Of these four delays, the first and second are the longest. This is due to the time necessary to ensure a new sample is obtained and the slurry settles on the sight glass 20. The third and fourth time delays are short since the frame grabber captures an image very quickly. The total cycle time is currently three seconds but may be extended minutes, hours, days, etc. This time was chosen as a balance between reliable statistics and minimal wear to the system 10.

In the invention, the overall analysis process of particulate material can be broken down into four parts: the physical acquisition of the particulate sample, control of the acquisition mechanism, the image capture, and the image analysis. The following description will be directed to describing the percentage of phosphate in a particulate composition which is an important aspect of the invention. The in-line determination of phosphate rock percentage begins with redirecting a portion of the phosphate slurry to the sampling apparatus. The water based slurry contains between 10 to 50 percent solids and has a particle size of from about 0.1 mm to about 1.0 mm. The sampling apparatus allows the solids to settle from the slurry so that an image of the settled particulates on the presentation window can be captured. After vortex sweeping of the sample window, the sample is then replaced by another. This process repeats about once every three to ten seconds. The acquisition rate is controlled by the PLC 28. The sample is photographed by camera 26 as a color-analog video image, while lit by a high intensity light. The image is transmitted to a video capture card installed in the computer 30. The capture card grabs the image and stores it in RAM for processing. The image processing program determines the phosphate content by performing a gray scale histogram. The last fifteen results are averaged and the phosphate content is reported once every minute. The results are saved to hard drive.

As described, the vortex sampler assembly is constructed of abrasive-resistant piping 38, a sight-glass assembly 20, a pressure orifice 42 or restrictive pipe 43, and the actuating valve 36 for sample acquisition and control. The slurry flow stream 48 travels through a two-inch inside diameter (ID) pipe 16 to the sight glass assembly cavity 18 and sample presentation window 20. The flow travels around the vortex tube 40 and out of the sight glass assembly to the pressure orifice 42. When a new image is required on the sight glass imaging window, the bypass valve 36 is opened which redirects the flow through the vortex tube 40 for picking up and sweeping away the sample. This redirection is created by the pressure differential across the orifice 42. The flow path of this redirected flow causes a vortex to form above the imaging window. This vortex ensures a fast and complete removal of the old sample from window 20. The rapid deposition of the next image sample is facilitated by the change in flow direction when the valve is returned to the closed position 37. The closing of the bypass valve above the imaging window 20 causes the vortex to stop immediately and the sample to deposit into the stagnation zone of the sight glass assembly. The new image is ready to be captured. The total cycle time for vortex sampler assembly is approximately three seconds.

The sample acquisition mechanism is controlled by the PLC 28 which includes a microprocessor having ten inputs and eight relayed outputs. The PLC package comes with a hand-held programmer unit to program the microprocessor. The computer 30 communicates with the PLC by means of an RS-232 cable. The computer portion providing image capture and analysis hardware of the system can be further broken down into two main areas, the computer and frame-grabber. The software was written in the computer programming language which is conventional to such applications. The first program obtains the gray scale analysis of an image and could be automated. Additionally, Visual Basic was used to achieve an acceptable interface as well as the ability to analyze images. The Visual Basic can call C routines which run much faster, Visual Basic can be upgraded to version 5 which is supposed to be faster, or if a fast enough computer is obtained speeding up program execution might prove unnecessary.

In the evaluation of frame-grabbers, the Matrox Meteor was chosen. This card has the necessary speed, comes with a basic software developer kit allowing it to be controlled by Visual Basic, and has a powerful image analysis library. In addition, the Matrox Meteor supports up to four cameras at once. This allows upgrades for multiple camera applications. The number and size of phosphate particles and changes in sand matrix as shown in image 70 of FIG. 4 alter the mean gray scale values, and the blob analysis of these changes was incorporated into the software since the color bin distribution analysis was specialized in the way that it approached the problem. The human eye detects the black particles in a picture by clarifying the relative intensities at the boundaries. The routines are based on reading the image into a 640×480 array and manipulating the entire picture. Thus, phosphate content was determined using an integrated blob analysis into the analysis routines.

Figure 4:
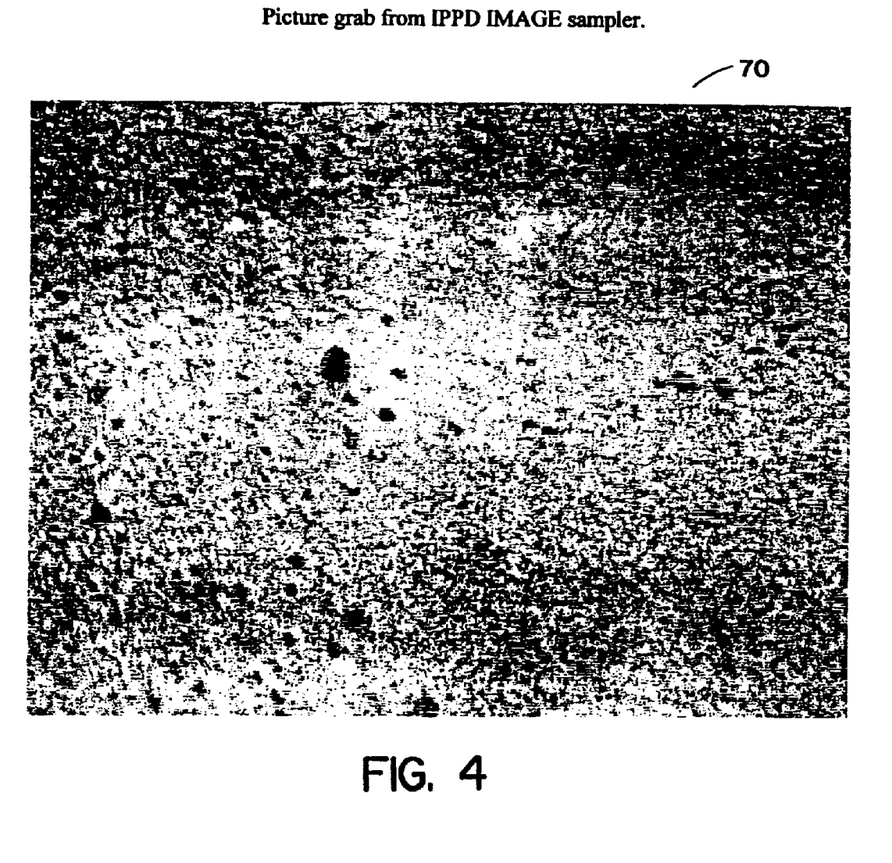
FIG. 4 shows a representative image captured for computer analysis for determining the level of dark particles in the sample representative of the phosphate content in the tailings stream.

A blob analysis routine was based on several available resources. The procedure calls for an edge detection filter to pass through the captured image 70. This filter looks for changes in the gradient and produces an image that has the dark patches outlined. The filter specifically takes advantage of the 256 gray shade range. The filter also utilizes a minor thresholding to obtain the outlined result. The next step in the procedure calls for a chain function to trace through the outlines and count the outlines that form complete loops. These loops are counted as blobs and the directions around the blobs are recorded. Another function determines the area of each blob by following the recorded directions (in a manner very similar to calculating the area under a curve). Since all blobs are not clean images, some are not found with the first pass of the chain function. Another function was adapted for the express purpose of cleaning up the remaining images. It specifically enters the interior of the remaining blobs and traces the inside of a blob where there is less visual noise.

Due to the long amount of time required for a chemical analysis of tailings sample, a dependable correlation between blob area and phosphate content was never obtained. To circumvent this limitation, a calibration procedure was introduced. The calibration button first grabs a series of pictures and performs the blob analysis routine on them. The result of this routine is written to disk. After the chemical analysis of the samples is obtained, the operator can input the BPL value into the calibration routine.

Figure 5:
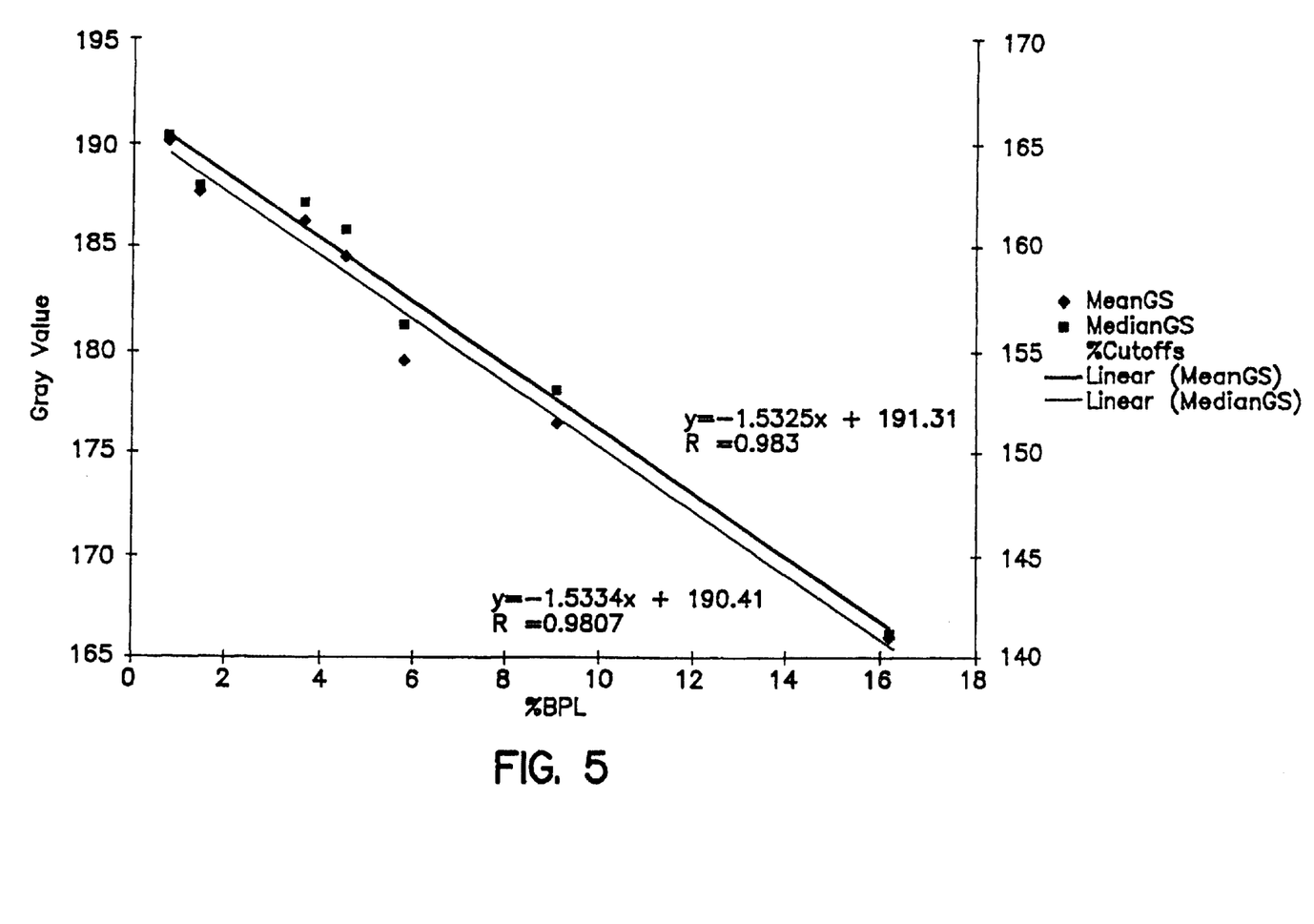
FIG. 5 is graph for determining the gray value versus %BPL correlation.

The calibration curve of FIG. 5 shows an $r^2$ value of 0.9807 for a linear fit of the experimental data under tight camera control. A similar correlation was tested for the median gray scale value. The mean was chosen for its sensitivity to skewed data. The mean gray value was determined for samples ranging from 0.6 to 16.2%BPL. This curve worked reliably for the bench scale model. The data is highly dependent upon information from calibration standards rather than individual images. With mean gray scale, the background is just as important as the black particles. This background color was discovered to change with sample material from different mining sites. Operator calibration was added to the software as a means of quickly adjusting this sensitivity. The slope of the correlation was assumed to be constant, whereas the intercept (or mean gray value of a pure sand image) could be changed whenever the operator calibrated the system. It was determined that a calibration between the blob areas and %BPL was a more accurate estimation of phosphate content.

In the blob analysis discussed above and provided as software program listing Appendix A, the image is scanned across each row until a black pixel is found. The chain code begins to search within a one-pixel neighborhood for another black pixel. The direction to each subsequent black pixel is recorded into the direction array and the previous pixel is erased so that it will not be found again. If no black pixel is found, the code searches for the darkest gray pixel in the same region. It was observed that one-pixel gaps occurred due to the thresholding in the filter. Lesser gradients were still passed through the filter as gray pixels. Chains that returned to their original pixels were considered blobs.

Figure 6:
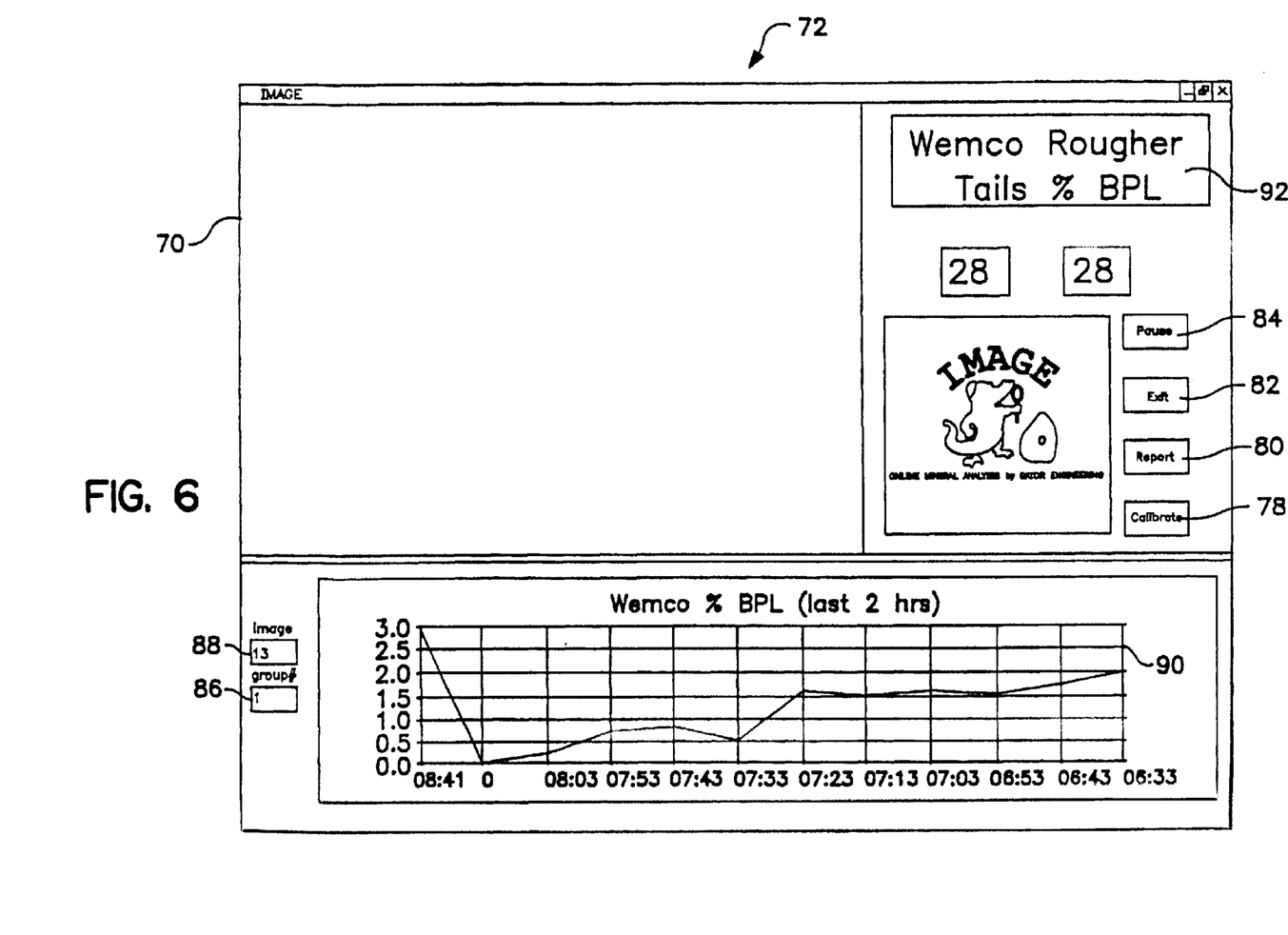
FIG. 6 shows a personal computer user interface for monitoring the phosphate content of the slurry.

FIG. 6 shows a personal computer user interface for monitoring the phosphate content of the slurry in a Windows PC environment. In particular, the computer screen 72 provides an image window for viewing the solid particulates being imaged 70. Running averages, herein respectively 1 minute and 10 minute running averages of the %BPL content in the tailing stream are indicated at reference numerals 74 and 76, respectively. The computer user interface 72 additionally includes a number of soft buttons, in particular a calibration button 78, report generation 80, exit 82 and pause 84. The sample group number is indicated in the lower left hand corner of the screen at reference 86, and the image of the group is identified by the image number 88, herein image number 13 being presented as the image 70 of the computer screen 72. The %BPL graph for the last two hours of operation is indicated at the lower portion of the computer screen as graph 90; as shown the graph 90 indicates a gradually decreasing %BPL content over time. Typically, it is desired that the %BPL be maintained below 3%, and thus the graph 90 provides a useful user interface for indicating when an alarm condition may be about to occur. As discussed above, light 46 is a power-on indicator for the PLC/camera unit, additionally the personal computer interface provides an alarm in number 92 which may change from a green color for proper operation to a red color to indicate a %BPL higher than what is desired, e.g., higher than 3%. As described, the computer user interface provides a useful interface for the operator to ascertain the trend of the tailing stream, and to allow for prompt corrective operation of the flotation cell for optimal performance.

While there has been illustrated and described a preferred embodiment of the present invention, it will be appreciated that modifications may occur to those skilled in the art, and it is intended in the appended claims to cover all those changes and modifications which fall within the true spirit and scope of the present invention.

What is claimed is:

1. An on-line sampling and image analysis system, comprising:

an inlet pipe for receiving a flow of a fluid media having particulates suspended therein;

a substantially horizontal sample presentation area positioned below the flow of the fluid media upon which a sample of the particulates from the fluid media is collected for viewing, a tube positioned in relation to said sample presentation area for removing the sample of the particulates deposited on said sample presentation area, wherein said tube comprises a media flow director which directs the media over the sample presentation area for removing sample of particulates away from said sample presentation area; and an outlet, wherein said media flow director returns the particulate sample collected at said sample presentation area to the fluid media at said outlet.

2. A system as recited in claim 1 wherein said media flow director is positioned above said sample presentation area.

3. A system as recited in claim 2 wherein said media flow director lifts the particulate sample away from said sample presentation area.

4. A system as recited in claim 1, comprising a characterizing detection device using an energy source to characterize the particulates of the fluid media, wherein the sample presentation area is pervious to the energy source employed.

5. A system as recited in claim 4, wherein the energy source comprises a light source for illuminating the sample presentation area, and wherein the sample presentation area comprises a window transparent to visible light.

6. A system as recited in claim 4, wherein the sample presentation area comprises a substantially planar surface to present the sample as having a planar surface to the characterizing detection device.

7. A system as recited in claim 1, wherein the sample presentation area is a window transparent to light and the system further comprises:
    a camera for imaging the sample of the particulates collected at said sample presentation area; and
    a computer for analyzing images provided by said camera to characterize the particulates of the fluid media.

8. A system as recited in claim 7, wherein said window comprises a substantially planar surface to present the sample as having a planar surface to the imaging camera.

9. An on-line sampling and image analysis system, comprising:
    an inlet pipe for receiving a flow of a fluid media having a solid content;
    a sample presentation window positioned below the flow of the fluid media upon which a sample of the solid content from the fluid media is substantially horizontal collected for viewing;
        a tube positioned above said sample presentation window for generating a vortex for at least partially removing the sample of the solid content deposited on said sample presentation window, wherein said tube for generating the vortex is positioned within the cavity of said pipe assembly extending above said sample presentation window through the flow of the fluid media defining an annulus in the cavity for receiving the sample of the solid content form the fluid media; and
        an outlet pipe through which the flow of the fluid media leaves the system, and wherein said tube for generating the vortex is coupled to a bypass pipe for returning the sample of solid content collected within the cavity on said sample presentation window to the fluid media at said outlet pipe.

10. A system as recited in claim 9, wherein said inlet pipe receives a fluid-solid mixture having phosphate and sand content.

11. A system as recited in claim 9 comprising a pipe assembly through which the fluid media is directed, said pipe assembly including a cavity below the directed flow of the fluid media, said sample presentation window being positioned at the bottom of said cavity for collecting the sample of the solid content from the fluid media in the cavity of said pipe assembly for viewing.

12. A system as recited in claim 9 comprising means for providing a differential pressure between said bypass pipe and the flow of the fluid media towards said outlet pipe for generating the vortex in said tube coupled to said bypass pipe.

13. A system as recited in claim 9 comprising a differential pressure orifice in the flow of the fluid media towards said outlet pipe for decreasing the pressure from fluid flow through said bypass pipe.

14. A system as recited in claim 9 comprising a pinch valve in said bypass pipe for actuating the vortex in said tube coupled to said bypass pipe.

15. A system as recited in claim 14, further comprising:
    a camera for imaging the sample of the solid content collected at said sample presentation window; and
    a computer for analyzing images provided by said camera to characterize the solid content of the fluid media.

16. A system as recited in claim 15 comprising a programmable logic controller (PLC) coupled to said computer, said camera, and said pinch value for sequencing the operation of said system for removing deposited solid content samples allowing for the collection of subsequent samples in which the vortex tube provides a bypass to return samples to the flow downstream of the sample presentation window for continuous operation without interruption of the flow in the sampling line.

17. A system as recited in claim 9, wherein said sample presentation window comprises a quartz sign glass, said system further comprising a quartz sign glass, said system further comprising a fiber optic ring light source for illuminating said sample presentation window for imaging the sample of the solid content collected with said camera.

18. An on-line sampling and image analysis system, comprising:
    means for receiving a fluid media having particulates solid suspended therein;
    means for collecting a substantially horizontal sample of the solid content from the fluid media;
    means for optically detecting the sample of the solid content collected at said means for collecting;
    means for analyzing the optically detected data provided by said means for imaging to characterize the solid content of the fluid media; and
        means for generating a vortex for at least partially removing the sample of the solid content collected at said means for collecting, wherein said vortex generating means sweeps the sample of the solid content collected from said means for collecting; and
        an outlet, and wherein said vortex generating means returns the sample of the solid content collected at said means for collecting to the fluid media at said outlet.

19. A system as recited in claim 18, wherein said receiving means receives a gas having a solid content.

20. A system as recited in claim 18, wherein said receiving means receives a liquid having a solid content.

21. An on-line sampling and imaging presentation enclosure, comprising:
    a substantially transparent sample presentation area disposed in the enclosure;
    at least one two-way opening in the enclosure disposed above the sample presentation area, which at least one two-way opening is operably coupled to a directed flow of fluid media such that the fluid media can both enter the enclosure and exit the enclosure via the two-way opening;
    at least one one-way opening in the enclosure disposed above the sample presentation area, which at least one one-way opening is operably coupled to a directed flow of cleansing fluid media such that the cleansing fluid media can enter the enclosure and substantially cleanse the sample presentation area.

22. The on-line sampling and imaging presentation enclosure of claim 21 wherein the cleansing fluid media is comprised of the directed flow of fluid media.

23. The on-line sampling and imaging presentation enclosure of claim 21 wherein the substantially transparent sample presentation area is disposed in a bottom end of the enclosure.

24. The on-line sampling and imaging presentation enclosure of claim 21 wherein the at least one two-way opening comprises a single annular opening.

25. The on-line sampling and imaging presentation enclosure of claim 24 wherein the at least one one-way opening comprises a tube.

26. The on-line sampling and imaging presentation enclosure of claim 25 wherein the tube is disposed through the annular opening.

27. The on-line sampling and imaging presentation enclosure of claim 26 wherein the tube is centrally disposed through the annular opening.

28. The on-line sampling and imaging presentation enclosure of claim 25 wherein the tube has an outlet that is disposed proximal to the sample presentation area.

29. A method of providing a sample of solid content in a fluid media for imaging analysis comprising:

providing a sampling presentation enclosure having a substantially transparent sample presentation area;

providing a first opening in the sampling presentation enclosure;

introducing the fluid media into the sampling presentation enclosure through the first opening such that at least some solid content in the fluid media will become deposited upon the substantially transparent sample presentation area through gravitational depositing to provide an imaging sample;

introducing the fluid media into the sampling presentation enclosure and towards the imaging sample through a media flow director to remove at least a substantial portion of the imaging sample from the substantially transparent sample presentation area;

evacuating the fluid media from the sampling presentation enclosure through the first opening.

30. The method of claim 29 wherein introducing the fluid media into the sampling presentation enclosure includes introducing the fluid media from a directed flow of fluid media into the sampling presentation enclosure.

31. The method of claim 30 wherein evacuating the fluid media includes returning the fluid media to the directed flow of fluid media.

32. The method of claim 29 wherein providing a sampling presentation enclosure having a substantially transparent sample presentation area includes providing a sampling presentation enclosure having a substantially transparent and substantially horizontal sample presentation area.

* * * * *